United States Patent
Flechsig et al.

(10) Patent No.: US 10,555,530 B2
(45) Date of Patent: Feb. 11, 2020

(54) BIOCIDE COMPOSITIONS BASED ON CALCIUM FLUORIDE AS WELL AS USES THEREOF

(71) Applicant: Flechsig Patent Company LLC, Cham (CH)

(72) Inventors: Frank Flechsig, Wohlen (CH); Thomas Flechsig, Hermetschwil-Staffeln (CH)

(73) Assignee: FLECHSIG PATENT COMPANY, LLC, Cham (CH)

( * ) Notice: Subject to any disclaimer, the term of this patent is extended or adjusted under 35 U.S.C. 154(b) by 0 days.

(21) Appl. No.: 15/306,075

(22) PCT Filed: Apr. 16, 2015

(86) PCT No.: PCT/EP2015/058231
§ 371 (c)(1),
(2) Date: Oct. 21, 2016

(87) PCT Pub. No.: WO2015/162049
PCT Pub. Date: Oct. 29, 2015

(65) Prior Publication Data
US 2017/0042161 A1    Feb. 16, 2017

(30) Foreign Application Priority Data

Apr. 25, 2014    (WO) ................ PCT/EP2014/001112

(51) Int. Cl.
| | | |
|---|---|---|
| *A01N 25/00* | (2006.01) | |
| *A01N 59/10* | (2006.01) | |
| *A01N 37/10* | (2006.01) | |
| *A61K 33/16* | (2006.01) | |
| *A01N 37/08* | (2006.01) | |
| *A01N 47/44* | (2006.01) | |
| *A01N 33/12* | (2006.01) | |
| *A01N 35/02* | (2006.01) | |
| *A01N 59/06* | (2006.01) | |
| *A61K 31/11* | (2006.01) | |
| *A61K 31/14* | (2006.01) | |
| *A61K 31/19* | (2006.01) | |
| *A61K 31/192* | (2006.01) | |
| *A61K 31/616* | (2006.01) | |
| *A61K 31/785* | (2006.01) | |
| *A61K 33/06* | (2006.01) | |
| *A61K 47/36* | (2006.01) | |

(52) U.S. Cl.
CPC ............ *A01N 59/10* (2013.01); *A01N 33/12* (2013.01); *A01N 35/02* (2013.01); *A01N 37/08* (2013.01); *A01N 37/10* (2013.01); *A01N 47/44* (2013.01); *A01N 59/06* (2013.01); *A61K 31/11* (2013.01); *A61K 31/14* (2013.01); *A61K 31/19* (2013.01); *A61K 31/192* (2013.01); *A61K 31/616* (2013.01); *A61K 31/785* (2013.01); *A61K 33/06* (2013.01); *A61K 33/16* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 4,917,901 | A | 4/1990 | Bourbon et al. |
| 5,942,218 | A | 8/1999 | Kirschner et al. |
| 5,990,174 | A | 11/1999 | Henry |
| 8,445,030 | B2 | 5/2013 | Voegeli et al. |
| 9,050,443 | B2 | 6/2015 | Knill et al. |
| 2008/0226566 | A1 | 9/2008 | Poth et al. |
| 2011/0064829 | A1* | 3/2011 | Voegeli ............... A61K 31/616 424/661 |

(Continued)

FOREIGN PATENT DOCUMENTS

| | | |
|---|---|---|
| CA | 1326446 C | 1/1994 |
| CN | 87103752 A | 9/1988 |

(Continued)

OTHER PUBLICATIONS

English language abstract for JP 2006124293 A (2006).

(Continued)

*Primary Examiner* — Susan T Tran
(74) *Attorney, Agent, or Firm* — Caesar Rivise, PC

(57) ABSTRACT

The present invention relates to improved biocide compositions based on calcium fluoride which are suitable for a broad range of applications including surface disinfectants, additives to construction materials and paints, antiseptic medical and cosmetic formulations, as a crop protection product and as a fast-acting disinfectant. The biocide composition of the invention comprise at least the following components: a) calcium fluoride b) a salicylic acid ester c) at least one organic acid selected from the group comprising or consisting of cinnamic acid, rosmarinic acid, vanillic acid, ascorbic acid, abscisic acid, mandelic acid, mevalonic acid, aspartic acid, salicylic acid, fumaric acid, isocitric acid, gallic acid, quinic acid, boswellic acid, carnosic acid, chlorogene acid, caffeic acid, other hydroxycarboxylic acids, or a salt or ester thereof, or thymol or citronellal. d) a cationic polymer and/or natural sea salt or a synthetic equivalent thereof and/or a cationic tenside, e) water. In preferred embodiments, the cationic polymer is selected from the group comprising or consisting of a poly(alkylene)guanidin or -biguanidin, or octenidin, and the organic acid is cinnamic acid and/or quinic acid.

13 Claims, No Drawings

(56) References Cited

U.S. PATENT DOCUMENTS

2014/0163485 A1\* 6/2014 Knill ................ A61F 13/00063
604/304

FOREIGN PATENT DOCUMENTS

| IE | 60364 B1 | 7/1994 |
|---|---|---|
| JP | 6322023 A | 1/1988 |
| JP | 04264009 A | 9/1992 |
| JP | 08510454 A | 11/1996 |
| JP | 2005002087 A | 1/2005 |
| JP | 2006124293 A | 5/2006 |
| WO | 2007051546 A1 | 5/2007 |
| WO | 2011141454 A1 | 11/2011 |
| WO | 2012104718 A2 | 8/2012 |

OTHER PUBLICATIONS

Cheng et al. "Antibacterial and physical properties of calcium—phosphate and calcium—fluoride nanocomposites with chlorhexidine." Dental materials 28.5 (2012): 573-583.
International Search Report for PCT/EP2015/058231 dated Jun. 29, 2015.
English Abstract for JP 2005002087 A (2005).
English Abstract of WO 8707143 A1 (1987).

\* cited by examiner

BIOCIDE COMPOSITIONS BASED ON CALCIUM FLUORIDE AS WELL AS USES THEREOF

BACKGROUND

The present invention relates to improved biocide compositions based on calcium fluoride which are suitable for a broad range of applications including the provision of antimicrobial activity on living tissue/skin, such as medical antiseptics, the provision of antimicrobial activity on other surfaces, such as general disinfectants in medical and non-medical fields, and/or the provision of antimicrobial activity or prevention of microbial activity, in particular fungal activity, in non-living objects, such as additives to construction materials and paints.

Generally, it is desired to have fast acting and persistent antiseptics and disinfectants.

Antiseptics or disinfectants are usually considered as "fast acting" if they achieve a significant reduction of the number of target microorganisms in a time period of less than minutes following application of the antiseptic.

The term "persistence" relates to the ability of the antiseptic to maintain its antimicrobial activity once it is applied and is connected with the retention of or binding of the agent on the respective surface, e.g. the stratum corneum of the skin, after partial evaporation and after rinsing. The persistence can be measured by the time required for the microflora to be restored to the baseline before the application.

Currently, there are several very fast acting antiseptics, effective within 20 seconds against pathogenic microorganisms, commercially available. Most of these antiseptics are based on alcohols, iodine solutions or chlorides. However, all the conventional fast acting antiseptics cannot prevent fast repopulation of the treated surface, such as skin. In particular in the latter case this effect is at last partially due to the fact that the natural body protection (fatty acids, presence of balanced salts, regulated pH etc.) against microbial invasions has also been destroyed.

U.S. Pat. No. 8,445,030 B2 discloses antiseptic or disinfectant compositions based on calcium fluoride which are both persistent and fast acting. In these compositions, the mineral calcium fluoride acts as the persistent component which sticks to the skin or surface for long periods and releases its antimicrobial acting fluorine ions only on "demand", such as in a warm and moist environment. This reference further discloses that highly toxic antiseptic compounds, such as hypochlorite or hydrogen peroxide, are added in a very low percentage in order to initiate and amplify fast antiseptic action on microorganisms.

It is also disclosed that other antimicrobial agents such as ethanol, salicylic acid esters, cinnamic acid, quinic acid, citric acid may be added to improve the antimicrobial efficacy of the claimed compositions.

However, in view of the typical presence of aggressive and toxic components such as hypochlorite or hydrogen peroxide, albeit in low concentrations, in said antiseptics, there is still a demand for further improved compositions which do not require the presence of hypochlorite or hydrogen peroxide and show the same or even better performance as that exhibited by the compositions of U.S. Pat. No. 8,445,030 B2.

In this respect, WO 2012/104718 A2 discloses that the presence of long-chain polymers (MW typically 40.000 or more) which provide a porous sponge-like structure, protecting the underlying and securing the reservoir against mechanical abrasion and wash-off, in a calcium fluoride based composition results in an effective water-based antiseptic spray. However, this document provides only a rather general teaching and does not disclose specific polymers and specific compositions for different applications comprising the same.

In view of this prior art, the object underlying the present invention is to provide further improved and optimized specific biocide compositions based on calcium fluoride which are essentially non-toxic, show an excellent antimicrobial performance, long-term stability, and are advantageously applicable for a broad range of medical and non-medical applications.

This object is achieved by the composition of the invention.

DESCRIPTION OF THE INVENTION

The present invention provides a biocide composition according to claim 1 comprising at least the following components:
a) calcium fluoride
b) a salicylic acid ester
c) at least one organic acid selected from the group comprising or consisting of cinnamic acid, rosmarinic acid, vanillic acid, ascorbic acid, abscisic acid, mandelic acid, mevalonic acid, aspartic acid, salicylic acid, fumaric acid, isocitric acid, gallic acid, quinic acid, boswellic acid, carnosic acid, chlorogene acid, caffeic acid, other hydroxyl carboxylic acids, or a salt or ester thereof, or thymol or citronellal,
d) a cationic polymer and/or natural sea salt or a synthetic equivalent thereof and/or a cationic tenside,
e) water.

The calcium fluoride ($CaF_2$) of component a) may be a natural occurring mineral, e.g. fluorspar, or a synthetic equivalent thereof. The particle size may vary, depending on the specific formulation and their intended use, and will be typically in a range from 0.25-5.0 μm, preferably 0.5-2.5 μm. The particle fineness can be adjusted as desired by milling.

Advantageously, $CaF_2$ has a pH of 5.4 which is in the range of normal skin (typically 5.4-5.5). Thus, it does not degrade the self-defense mechanism of the skin, contrary to basic soaps.

The salicylic acid ester may be any ester suitable, in particular any ester which is water soluble and, in particular for medical applications, non-toxic and pharmacologically/physiologically acceptable in the concentrations used. Preferably, said ester is salicylic acid acetate (acetylsalicylic acid) or another ester of the hydroxyl group of salicylic acid with a lower alkyl carboxylic acid such as a $C_{3-17}$ carboxylic acid, more specifically a $C_{3-10}$ carboxylic acid.

The organic acid of component c) may be principally any carboxylic acid having antimicrobial activity which is non-toxic in the required concentration ranges.

Preferably the organic acid is selected from the group comprising or consisting of cinnamic acid, rosmarinic acid, vanillic acid, ascorbic acid, abscisic acid, mandelic acid, mevalonic acid, aspartic acid, salicylic acid, fumaric acid, isocitric acid, gallic acid, quinic acid, boswellic acid, carnosic acid, chlorogene acid, caffeic acid, other hydroxycarboxylic acids. A salt or ester of one or more of these compounds may be used as well.

Cinnamic acid represents a preferred component of the claimed composition. However, it is possible to substitute this compound by one or more of rosmarinic acid, vanillic acid, ascorbic acid, abscisic acid, mandelic acid, mevalonic acid, aspartic acid, salicylic acid, fumaric acid, isocitric acid, gallic acid or thymol or to combine cinnamic acid with one or more of these alternative compounds.

Also, a quinic acid, in particular D-(−)-quinic acid, represents a preferred component of the claimed composition. However, it is possible to substitute this compound by one or more of boswellic acid, carnosic acid, chlorogene acid, caffeic acid or to combine quinic acid with one or more of these alternative compounds.

The cationic polymer of component d) may be principally any cationic polymer having antimicrobial activity which is non-toxic for humans in the required concentration ranges for the respective applications. Preferably the cationic polymer is selected from the group comprising or consisting of a poly(alkylene)guanidin or -biguanidin, octenidin. Specific non-cationic polymers with antimicrobial activity such as polyethylene glycol may also be a component of the inventive compositions. Furthermore, it is assumed that the cationic group of the cationic polymer is advantageously less reactive with regard to the organic acids of the claimed composition.

More specifically, the cationic polymer is a poly(alkylene)-guanidin or -biguanidin having a molecular weight in the range from 1,000 to 10,000, preferably 1,000 to 4,000 Dalton.

In especially preferred embodiments, the cationic polymer is poly(hexamethylen)guanidin (PHMG) or poly(hexamethylen)biguanidin (PHMB). It is assumed that the surprisingly good results of the claimed composition is because the cationic polymer supports in particular the antimicrobial performance of calcium fluoride ($CaF_2$). For example, PHMG is known as having a destructive impact on the membrane function of bacterial cells.

The natural sea salt or synthetic equivalent thereof may be any salt composition which provides the desired benefits. Typically, these salts have an electrolytic composition which promotes the constructive metabolism of the skin. Preferably, the sea salt is salt from the Dead Sea or a synthetic equivalent (having the same major components) thereof.

Preferably, the cationic tenside is selected from the group comprising or consisting of benzalkonium chloride, distearyldimethylammonium chloride, esterquat, cetrimonium bromide, cetylpyridinium chloride or any possible mixture thereof. The usage of the cationic tenside has proven to have a synergistic effect with calcium fluoride ($CaF_2$) towards a notably fast-acting antimicrobial, in particular virucide, activity. Advantageously, the cationic tenside is used for providing a fast-acting disinfectant. It is assumed that the surprisingly good results of the claimed composition is based on the surface-active properties of the cationic tenside supporting in particular the performance of calcium fluoride ($CaF_2$). Furthermore, it is assumed that the cationic group of the cationic tenside is advantageously less reactive with regard to the organic acids of the claimed composition.

More preferably one of the following salts KCl, $MgCl_2$, $MgSO_4$, NaCl, NaF is used in combination with the cationic tenside in order to improve the antimicrobial activity, in particular the virucide activity against unveiled viruses.

Optionally, the claimed composition may also comprise alginate compounds and a rheological agent, such as xanthan gum. These additives are preferably present in compositions which are used for wound care products, such as wound gels, wound dressings etc., or in cosmetic formulations.

The alginate may be present as calcium alginate or other alginate compounds known in the art. Short-chain alginates, preferably comprising 180 to 500 saccharide units, such as 150 to 300 units or 150 to 200 units, are preferred. Alginate supports healing processes i.a. by promoting the constructive metabolism of the skin.

It was especially surprising that the combination of alginate and (sea) salt improves the performance of the claimed composition with respect to its skin regenerating properties in a synergistic manner.

Rheological agents such as xanthan gum are used to adjust the viscosity and consistency of the respective composition as desired. Xanthan gum is a stable and neutral thickener in the acidic range. The skilled artisan will recognize that other agents with the same essential properties could be used as well.

The concentrations of the various compounds in the claimed biocide compositions may vary considerably depending from the respective specific application and the presence of other specific components.

Typically, component a) is present in a range from 5 ppm to 5.000 ppm, preferably from 10 ppm to 3.000 ppm, component b) is present in a range from 5 ppm to 80.000 ppm, preferably from 500 ppm to 60.000 ppm, component c) is present in a range from 5 ppm to 80.000 ppm, preferably from 10 ppm to 60.000 ppm, component d) is present in a range from 5 ppm to 50.000 ppm, preferably from 50 ppm to 30.000 ppm, component e) is present in a range from 785.000 ppm to 999.980 ppm, preferably from 900.000 ppm to 999.000 ppm, and optionally component f) is present in a range from 5 ppm to 30.000 ppm, preferably from 500 ppm to 3000 ppm and/or component g) is present in a range from 500 ppm to 15.000 ppm, preferably from 1000 ppm to 8000 ppm.

Suitable general ranges for a number of essential or preferred specific components are compiled in the following Table 1.

TABLE 1

| Component | Amount (in ppm of the total composition) |
| --- | --- |
| Acetylsalicylic acid | 5 ppm to 80.000 ppm |
| Cinnamic acid | 5 ppm to 15.000 ppm |
| D-(−)-Quinic acid | 5 ppm to 40.000 ppm |
| Ascorbic acid | 5 ppm to 80.000 ppm |
| Carnosic acid | 5 ppm to 40.000 ppm |
| Calcium fluoride | 5 ppm to 5.000 ppm |
| Cationic polymer | 5 ppm to 40.000 ppm |
| Dead Sea salt | 5 ppm to 50.000 ppm |
| Alginate | 5 ppm to 30.000 ppm |

Preferred ranges for a number of essential or preferred components which are especially suited for an antiseptic or "physiologic" disinfectant, i.e. intended for contacting living tissue/skin, are compiled in the following Table 2.

TABLE 2

| Component | Amount (in ppm of the total composition) |
| --- | --- |
| Acetylsalicylic acid | 500 ppm to 2.000 ppm |
| Cinnamic acid | 500 ppm to 1.000 ppm |
| D-(−)-Quinic acid | 50 ppm to 1.000 ppm |
| Ascorbic acid | 5 ppm to 1.000 ppm |
| Carnosic acid | 5 ppm to 500 ppm |
| Calcium fluoride | 10 ppm to 500 ppm |
| Cationic polymer | 50 ppm to 500 ppm |

An exemplary biocide composition which is essentially suited for an antiseptic or physiologic disinfectant as define above comprises or consists of the following components:
a) calcium fluoride in an amount in the range from 10 ppm to 500 ppm,
b) a salicylic acid ester, preferably, acetylsalicylic acid, in an amount in the range from 500 ppm to 2000 ppm,
c1) cinnamic acid in an amount in the range from 500 ppm to 2.000 ppm
c2) quinic acid in an amount in the range from 50 ppm to 1.000 ppm,
d) a cationic polymer in an amount in the range from 50 ppm to 500 ppm,
e) water in an amount in the range from 990.500 to 998.890.

Preferred ranges for a number or essential or preferred components which are especially suited for a (non-physiologic) disinfectant for surface treatment of other surfaces than skin or living tissue are compiled in the following Table 3.

TABLE 3

| Component | Amount (in ppm of the total composition) |
| --- | --- |
| Acetylsalicylic acid | 500 ppm to 2.500 ppm |
| Cinnamic acid | 500 ppm to 1.500 ppm |
| D-(−)-Quinic acid | 50 ppm to 2.000 ppm |
| Carnosic acid | 5 ppm to 1.000 ppm |
| Calcium fluoride | 10 ppm to 1000 ppm |
| Cationic polymer | 50 ppm to 4.000 ppm |

An exemplary biocide composition which is especially suited for a non-physiologic disinfectant for surface treatment comprises or consists of the following components:
a) calcium fluoride in an amount in the range from 10 ppm to 1000 ppm,
b) a salicylic acid ester, preferably, acetylsalicylic acid, in an amount in the range from 500 ppm to 2500 ppm,
c1) cinnamic acid in an amount in the range from 500 ppm to 1.500 ppm
c2) quinic acid in an amount in the range from 50 ppm to 2.000 ppm,
d) a cationic polymer in an amount in the range from 50 ppm to 4000 ppm,
e) water in an amount in the range from 989.000 to 998.890.

Preferred ranges for a number of essential or preferred components which are especially suited for a medical formulation for antiseptic wound care or the treatment of diseases caused by pathogens (such as viruses, bacteria, fungi) are compiled in the following Table 4.

TABLE 4

| Component | Amount (in ppm of the total composition) |
| --- | --- |
| Acetylsalicylic acid | 500 ppm to 2.500 ppm |
| Cinnamic acid | 500 ppm to 1.500 ppm |
| D-(−)-Quinic acid | 500 ppm to 2.000 ppm |
| Ascorbic acid | 800 ppm to 2.000 ppm |
| Calcium fluoride | 16 ppm to 3.000 ppm |
| Dead Sea salt | 200 ppm to 3.000 ppm |
| Alginate | 500 ppm to 3.000 ppm |
| Xanthan gum | 1.000 ppm to 8.000 ppm |

Preferred ranges for a number of essential or preferred components which are especially suited for additives to construction materials and paints are compiled in the following Table 5.

TABLE 5

| Component | Amount (in ppm of the total composition) |
| --- | --- |
| Acetylsalicylic acid | 2500 ppm to 60.000 ppm |
| Cinnamic acid | 500 ppm to 10.000 ppm |
| Carnosic acid | 200 ppm to 5.000 ppm |
| Calcium fluoride | 16 ppm to 5.000 ppm |
| Cationic polymer | 200 ppm to 30.000 ppm |

An exemplary biocide composition which is especially suited for additive for construction materials and paints comprises or consists of the following components:
a) calcium fluoride in an amount in the range from 160 ppm to 5.000 ppm,
b) a salicylic acid ester, preferably acetylsalicylic acid, in an amount in the range from 2.500 ppm to 60.000 ppm,
c1) cinnamic acid in an amount in the range from 500 ppm to 10.000 ppm,
c2) carnosic acid in an amount in the range from 0 ppm to 5.000 ppm,
d) a cationic polymer in an amount in the range from 50 ppm to 30.000 ppm,
e) water in an amount in the range from 989.000 to 998.890.
f) $CaSO_4$ in an amount in the range from 1000 ppm to 5000 ppm.

An exemplary biocide composition which is especially suited for additive for a medical formulation for antiseptic wound care or the treatment of diseases caused by pathogens (such as viruses, bacteria fungi) comprises or consists of the following components:
a) calcium fluoride in an amount in the range from 16 ppm to 3.000 ppm,
b) a salicylic acid ester, preferably acetylsalicylic acid, in an amount in the range from 500 ppm to 3.000 ppm,
c1) cinnamic acid in an amount in the range from 500 ppm to 1.500 ppm,
c2) quinic acid in an amount in the range from 500 ppm to 2.000 ppm,
d) a natural salt from the Dead Sea or a synthetic equivalent thereof in an amount in the range from 200 ppm to 3.000 ppm,
e) water in an amount in the range from 976.500 to 997.000.
f) alginate in an amount in the range from 500 ppm to 3.000 ppm,
g) xanthan gum in an amount in the range from 1.000 ppm to 8.000 ppm.

This composition or a similar composition may also be used in cosmetic formulations, in particular skin care or hair care products.

Preferred ranges for a number of essential or preferred components which are especially suited for a crop protection product are compiled in the following Table 6.

TABLE 6

| Component | Amount (in ppm of the total composition) |
| --- | --- |
| Calcium fluoride | 5 to 5'000 |
| Acetylsalicylic acid | 5 to 80'000 |
| Organic acid | 5 to 80'000 |
| Cationic polymer | 5 to 50'000 |
| Water | 785'000 to 999,980 |
| Alginate | 500 to 3'000 |
| Salt | 200 to 3'000 |

Preferred ranges for a number of essential or preferred components which are especially suited for a fast-acting disinfectant are compiled in the following Table 7.

TABLE 7

| Component | Amount (in ppm of the total composition) |
|---|---|
| Calcium fluoride | 10 to 500 |
| Acetylsalicylic acid | 500 to 2'500 |
| Organic acid | 50 to 1'000 |
| Cationic tenside | 5 to 20'000 |
| Water | 896'000 to 999'175 |
| Alginate | 250 to 50'000 |
| Salt | 10 to 30'000 |

It has been proven that, advantageously, alginate improves the long-time activity of the fast-acting disinfectant.

Advantageously, the biocide compositions of the present invention are free of ethanol, propanol, hypochlorite or hydrogen peroxide.

The claimed aqueous biocide compositions and gels are fast acting, persistent and long term-stable, such as for a time period of at least 3 years.

As already mentioned above, the biocide compositions of the invention are suitable for a broad range of applications including the provision of antimicrobial activity on living tissue/skin, such as antiseptic medical formulations or physiologic disinfectants, and/or the provision of antimicrobial activity or prevention of microbial activity, in particular fungal activity, in non-living objects, such as additives to construction materials and paints.

Consequently more specific aspects of the invention relate to the use of such compositions as a physiologic disinfectant as a general non-physiologic surface disinfectant, as an additive for construction materials and paints, as an antiseptic medical formulation for the treatment of diseases caused by pathogens such as bacteria, fungi and viruses, and to the use in an antiseptic wound gel or an antiseptic wound dressing. A still further aspect of the invention relates to the use of such compositions in an antiseptic cosmetic formulation.

Further, closely related aspects of the invention relate to a disinfectant comprising or consisting of such compositions for the treatment of physiologic surfaces, i.e. surfaces which comprise living tissue or skin, or for non-physiologic surfaces, i.e. surfaces which are not comprising living tissue or skin, to an additive, in particular antimycotic additive, for construction materials and paints, which additive comprises or consists of such compositions, to an antiseptic wound gel comprising or consisting of such composition, to an antiseptic cosmetic formulation, in particular a skin care or hair care product, which comprises or consists of such a composition, and to an antiseptic medical formulation for the treatment of diseases caused by pathogens such as bacteria, fungi and viruses, comprising or consisting of such a composition.

A still further aspect of the invention relates to a method for treating diseases, in particular diseases which affect the skin, caused by pathogens such as bacteria, fungi and viruses which method comprises the topical application of an antiseptic formulation comprising or consisting of such a composition onto skin or tissue of a subject suffering from such a disease.

The composition of the present invention may be used in variety of forms, as appropriate for the respective application. The may be used as an aqueous solution or suspension, including a composition suitable for application as a spray, as a gel or cream, etc. They may be used as such or combined with other active principles or carrier materials (e.g. in a wound-dressing).

The present invention is further illustrated by the following non-limiting Examples.

EXAMPLE 1

A Biocide Composition for Use as a Physiologic Disinfectant or Antiseptic was Prepared by Mixing the Following Components in the Indicated Ratios

| Component | Amount (in ppm of the total composition) |
|---|---|
| Acetylsalicylic acid | 2.000 ppm |
| Cinnamic acid | 500 ppm |
| D-(−)-Quinic acid | 500 ppm |
| Calcium fluoride | 30 ppm |
| PHMG | 25 ppm |
| Citronellal | 25 ppm |
| Water | 996.920 ppm | and tested with respect to its performance.

The antimicrobial activity of the above indicated biocide composition was tested at 20° C. against the following microorganisms:

Bacteria: *Staphylococcus aureus* ATCC 6538 and *Pseudomonas aeruginosa* ATCC 15442, cultivated for 24-48 h at 36° C. on CASO agar Fungi: *Candida albicans* ATCC 10231, cultivated for 48-72 h at 30° C. on ME agar Fungal spores: *Aspergillus niger* (*A. brasiliensis*) ATCC 16404, cultivated for 48-72 h at 30° C. on ME agar Bacterial spores: *Bacillus subtilis* ATCC 6633, cultivated for 24-48 h at 36° C. on CASO agar

| Microorganism | Germ count after 1 min. (lg cfu/ml) | Reduction after 1 h (lg grades) | Germ count after 5 min. (lg cfu/ml) | Reduction after 5 min. (lg grades) |
|---|---|---|---|---|
| S. aureus Initial germ count 1.0 × 10⁹ cfu (colony forming units)/ml lg N = 9.00 | <2.00 | >7.00 | <2.00 | >7.00 |
| P. aeruginosa Initial germ count 1.83 × 10⁹ cfu/ml lg N = 9.26 | <2.00 | >7.26 | <2.00 | >7.26 |
| C. albicans Initial germ count 6.87 × 10⁶ cfu/ml lg N = 6.87 | <2.00 | >4.87 | <2.00 | >4.87 |
| A. niger Initial germ count 4.1 × 10⁶ cfu/ml lg N = 6.61 | 6.56 | 0.05 | <2.00 | >4.61 |
| B. subtilis Initial germ count 4.1 × 10⁶ cfu/ml lg N = 6.61 | 5.23 | 1.38 | 5.26 | 1.35 |

Summary: The tested biocide composition shows a strong activity against bacteria and yeasts already after a short impact time of 1 minute (meeting the VAH (Association for Applied Hygiene) requirements for a skin/hand disinfectant) and after 5 minutes also a strong effect against fungal and bacterial spores (which is not a VAH requirement for a skin/hand disinfectant).

EXAMPLE 2

A Biocide Composition for Use as a Non-Physiologic Surface Disinfectant was Prepared by Mixing the Following Components in the Indicated Ratios

| Component | Amount (in ppm of the total composition) |
| --- | --- |
| Acetylsalicylic acid | 2.000 ppm |
| Cinnamic acid | 500 ppm |
| D-(−)-Quinic acid | 500 ppm |
| Calcium fluoride | 30 ppm |
| PHMG | 25 ppm |
| Water | 996.945 ppm | and tested with respect to its performance.

EXAMPLE 3

A Biocide Composition for Use as an Antiseptic Medical Formulation for the Treatment of Diseases Caused by Pathogens (Bacteria, Fungi and Viruses) was Prepared by Mixing the Following Components in the Indicated Ratios

| Component | Amount (in ppm of the total composition) |
| --- | --- |
| Acetylsalicylic acid | 2.000 ppm |
| Cinnamic acid | 1.000 ppm |
| D-(−)-Quinic acid | 1.000 ppm |
| Calcium fluoride | 1.600 ppm |
| Dead Sea Salt | 1.000 ppm |
| Alginate | 1.500 ppm |
| Xanthan gum | 3.400 ppm |
| Water | 998.500 ppm | and tested with respect to its performance.

EXAMPLE 4

A Biocide Composition for Use as an Antimycotic Additive to Construction Materials and Paints was Prepared by Mixing the Following Components in the Indicated Ratios

| Component | Amount (in ppm of the total composition) |
| --- | --- |
| Acetylsalicylic acid | 10.000 ppm |
| Cinnamic acid | 5000 ppm |
| Calcium fluoride | 2000 ppm |
| PHMG | 20.000 ppm |
| Calcium sulphate | 2.000 ppm |
| Water | 961.000 ppm | added to paint in a desired concentration and tested with respect to its performance.

EXAMPLE 5

A Biocide Composition for Use in an Antiseptic Wound Gel was Prepared by Mixing the Following Components in the Indicated Ratios

| Component | Amount (in ppm of the total composition) |
| --- | --- |
| Acetylsalicylic acid | 2.000 ppm |
| Cinnamic acid | 1.000 ppm |
| D-(−)-Quinic acid | 1.000 ppm |
| Calcium fluoride | 1.600 ppm |
| Dead Sea Salt | 1.000 ppm |
| Alginate | 1.500 ppm |
| Xanthan gum | 3.400 ppm |
| Water | 988.500 ppm | and tested with respect to its performance.

EXAMPLE 6

A Biocide Composition for Use as a Crop Protection Product was Prepared by Mixing the Following Components in the Indicated Ratios

| Component | Amount (in ppm of the total composition) |
| --- | --- |
| Calcium fluoride | 50 |
| Acetylsalicylic acid | 2'500 |
| Cinnamic acid | 1'350 |
| PHMG | 5'550 |
| Water | 990'550 |

In particular, the antimicrobial activity of the above indicated biocide composition in a 50% dilution was tested against the following, typical harmful microorganisms in the agricultural field:

Bacterium: *Erwinia amylovora* Ea385, cultivated for 24 h at 27° C. on Nutrient Sucrose Agar/Broth; incubated for 1 h at 22° C.

Fungi: *Phytophtora infestans* M16, cultivated for 3 weeks at 20° C. on vegetable juice agar; incubated for 24 h at 20° C. and

*Venturia inaequalis*; incubated for 24 h at 20° C.

| Microorganism | Germ count after 1 h (lg cfu/ml) | Reduction after 1 h (lg grades) | Germ count after 24 h (lg cfu/ml) | Reduction after 24 h (lg grades) |
| --- | --- | --- | --- | --- |
| *Erwinia amylovora* Initial germ count $2.0 \times 10^8$ cfu (colony forming units)/ml lg N = 8.3 | <1.00 | 8 | — | — |
| *Phytophtora infestans* Initial germ count at least 100 sporangia/ microscope slide | — | — | <1.00 | 2 (nearly 100% reduction) |
| *Venturia inaqualis* Initial germ count at least 200 conidia/ microscope slide | — | — | <1.00 | 2 (over 99% reduction) |

EXAMPLE 7

A Biocide Composition for Use as a Fast-Acting Disinfectant was Prepared by Mixing the Following Components in the Indicated Ratios

| Component | Amount (in ppm of the total composition) |
|---|---|
| Calcium fluoride | 10 |
| Acetylsalicylic acid | 2'000 |
| Cinnamic acid | 1'000 |
| Benzalkonium chloride (BAC) | 40 |
| Water | 996'950 |

In particular, the antimicrobial activity of the above indicated improved disinfectant without a further dilution was tested at 20° C. against the following microorganisms:

Bacterium: *Staphylococcus aureus* ATCC 6538 and *Pseudomonas aeruginosa* ATCC 15442, cultivated for 24 to 48 h at 36° C. on casein-soy flour-peptone agar Fungal spores: *Candida albicans* ATCC 10231 and *Aspergillus niger* (*A. brasiliensis*) ATCC 16404, cultivated for 72 to 96 h at 30° C. on ME agar

| Microorganism | Germ count after 1 min (lg cfu/ml) | Reduction after 1 min (lg grades) | Germ count after 5 min. (lg cfu/ml) | Reduction after 5 min. (lg grades) |
|---|---|---|---|---|
| *S. aureus* Initial germ count $2.82 \times 10^7$ cfu (colony forming units)/ml lg N = 7.45 | <1.00 | >6.45 | <1.00 | >6.45 |
| *P. aeruginosa* Initial germ count $8.9 \times 10^7$ cfu/ml lg N = 7.95 | <1.00 | >6.95 | <1.00 | >6.95 |
| *C. albicans* Initial germ count $1.95 \times 10^6$ cfu/ml lg N = 6.29 | 2.95 | 3.34 | <1.00 | >5.29 |
| *A. niger* (*A. brasiliensis*) Initial germ count $2.20 \times 10^6$ cfu/ml lg N = 6.34 | 5.81 | 0.53 | 5.83 | 0.51 |

The invention claimed is:

1. A biocide composition comprising at least the following components:
   a) calcium fluoride in a range from 5 ppm to 5,000 ppm;
   b) a salicylic acid ester in a range from 5 ppm to 80,000 ppm;
   c) at least one organic acid selected from the group consisting of cinnamic acid, rosmarinic acid, vanillic acid, ascorbic acid, abscisic acid, mandelic acid, mevalonic acid, aspartic acid, salicylic acid, fumaric acid, isocitric acid, gallic acid, quinic acid, boswellic acid, carnosic acid, chlorogene acid, caffeic acid, other hydroxycarboxylic acids, salts and esters thereof, thymol and citronellal, wherein the at least one organic acid is present in a range from 5 ppm to 80,000 ppm;
   d) a poly(alkylene)guanidin in a range from 5 ppm to 50,000 ppm; and
   e) water in a range from 785,000 ppm to 999,980 ppm, wherein the biocide composition is effective for use as a crop protection product and is free of ethanol, propanol, hypochlorite and hydrogen peroxide.

2. The biocide composition according to claim 1, wherein the poly(alkylene)guanidin has a molecular weight in a range from 1,000 to 10,000 Dalton.

3. The biocide composition according to claim 1, wherein the poly(alkylene)guanidin is poly(hexamethylen)guanidin (PHMG).

4. The biocide composition according to claim 1, which further comprises
   f) alginate, and
   g) a rheological agent.

5. The biocide composition according to claim 4, wherein:
   component a) is present in a range from 5 ppm to 5,000 ppm,
   component b) is present in a range from 5 ppm to 80,000 ppm,
   component c) is present in a range from 5 ppm to 80,000 ppm,
   component d) is present in a range from 5 ppm to 50,000 ppm,
   component e) is present in a range from 785,000 ppm to 999,980 ppm,
   and optionally
   component f) is present in a range from 5 ppm to 30,000 ppm, and/or
   component g) is present in a range from 500 ppm to 15,000 ppm.

6. The biocide composition according to claim 5, wherein:
   component a) is present in a range from 10 ppm to 3,000 ppm,
   component b) is present in a range from 500 ppm to 60,000 ppm,
   component c) is present in a range from 10 ppm to 60,000 ppm,
   component d) is present in a range from 50 ppm to 30,000 ppm,
   component e) is present in a range from 900,000 ppm to 999,000 ppm,
   and optionally
   component f) is present in a range from 500 ppm to 3,000 ppm, and/or
   component g) is present in a range from 1,000 ppm to 8,000 ppm.

7. The biocide composition according to claim 4, wherein component f) is present in a range from 5 ppm to 30,000 ppm, and component g) is present in a range from 500 ppm to 15,000 ppm.

8. The biocide composition according to claim 1, comprising:
   a) calcium fluoride in an amount in a range from 10 ppm to 500 ppm,
   b) salicylic acid ester in an amount in a range from 500 ppm to 2000 ppm,
   c1) cinnamic acid in an amount in a range from 500 ppm to 2,000 ppm,
   c2) quinic acid in an amount in a range from 50 ppm to 1,000 ppm,
   d) the poly(alkylene)guanidin in an amount in a range from 50 ppm to 500 ppm, and e) water in an amount in a range from 990,500 to 998,900 ppm.

9. The biocide composition according to claim 1, comprising:
   a) calcium fluoride in an amount in a range from 10 ppm to 1000 ppm,
   b) salicylic acid ester in an amount in a range from 500 ppm to 2500 ppm,
   c1) cinnamic acid in an amount in a range from 500 ppm to 1,500 ppm,
   c2) quinic acid in an amount in a range from 50 ppm to 2,000 ppm,
   d) the poly(alkylene)guanidin in an amount in a range from 50 ppm to 4,000 ppm, and
   e) water in an amount in a range from 989,000 to 998,890 ppm.

10. The biocide composition according to claim 1, comprising:
    a) calcium fluoride in an amount in a range from 160 ppm to 5,000 ppm,
    b) salicylic acid ester in an amount in a range from 2,500 ppm to 60,000 ppm,
    c1) cinnamic acid in an amount in a range from 500 ppm to 10,000 ppm,
    c2) carnosic acid in an amount in a range from 0 to 5,000 ppm,
    d) the poly(alkylene)guanidin in an amount in a range from 200 ppm to 30,000 ppm,
    e) water in an amount in a range from 890,000 ppm to 996,640 ppm, and
    f) $CaSO_4$ in an amount in a range from 1000 ppm to 5000 ppm.

11. The biocide composition according to claim 4, comprising:
    a) calcium fluoride in an amount in a range from 16 ppm to 3,000 ppm,
    b) salicylic acid ester in an amount in a range from 500 ppm to 3,000 pp,
    c1) cinnamic acid in an amount in a range from 500 ppm to 1,500 ppm,
    c2) quinic acid in an amount in a range from 500 ppm to 2,000 ppm,
    d) the poly(alkylene)guanidin and natural salt from the Dead Sea or a synthetic equivalent thereof, wherein the natural salt is provided in an amount in a range from 200 ppm to 3,000 ppm,
    e) water in an amount in a range from 976,500 to 997,300,
    f) alginate in an amount in a range from 500 ppm to 3,000 ppm, and
    g) xanthan gum in an amount in a range from 1,000 ppm to 8,000 ppm.

12. A biocide composition according to claim 1, wherein the at least one organic acid is at least one member selected from the group consisting of cinnamic acid, rosmarinic acid, salicylic acid, quinic acid and salts and esters thereof.

13. A biocide composition according to claim 1, wherein the at least one organic acid is cinnamic acid, quinic acid and salts and esters thereof.

* * * * *